United States Patent
Sagan et al.

(10) Patent No.: US 8,909,312 B2
(45) Date of Patent: Dec. 9, 2014

(54) SIGNAL ACQUISITION CIRCUIT FOR DETECTING A WANTED SIGNAL IN THE PRESENCE OF AN UNWANTED SIGNAL

(75) Inventors: Didier Serge Sagan, San Diego, CA (US); Reghu Kunnath Rajan, San Diego, CA (US)

(73) Assignee: Microsemi Corporation, Aliso Viejo, CA (US)

( * ) Notice: Subject to any disclaimer, the term of this patent is extended or adjusted under 35 U.S.C. 154(b) by 575 days.

(21) Appl. No.: 13/109,364

(22) Filed: May 17, 2011

(65) Prior Publication Data

US 2012/0296185 A1 Nov. 22, 2012

(51) Int. Cl.
*A61B 5/1455* (2006.01)
*A61B 5/00* (2006.01)

(52) U.S. Cl.
CPC ............ *A61B 5/14551* (2013.01); *A61B 5/7203* (2013.01); *A61B 2560/0209* (2013.01)
USPC ............................ 600/336; 600/310; 600/323

(58) Field of Classification Search
USPC .................................................. 600/309–344
See application file for complete search history.

(56) References Cited

U.S. PATENT DOCUMENTS

| | | |
|---|---|---|
| 5,676,141 A | 10/1997 | Hollub |
| 2003/0036689 A1* | 2/2003 | Diab et al. ..................... 600/323 |
| 2004/0138572 A1 | 7/2004 | Thiagarajan |
| 2009/0154573 A1 | 6/2009 | Petersen |
| 2010/0087718 A1 | 4/2010 | Gonopolskiy et al. |
| 2011/0001963 A1 | 1/2011 | Durack |

FOREIGN PATENT DOCUMENTS

| | | |
|---|---|---|
| TW | 200537884 B | 6/2003 |
| TW | 201105950 A | 2/2011 |
| WO | 03003914 A1 | 1/2003 |

OTHER PUBLICATIONS

Sankman, Joseph, Transitioning from Analog to Digital in Medical Designs, RTC Magazine, Sep. 2010, pp. 42-45.
Hauske, Maximilian et al, "Artificial Lighting Interference on Free Space Photoelectric Systems," EMC'09/Kyoto, pp. 125-128, IEICE. Date:2009.

* cited by examiner

*Primary Examiner* — Eric Winakur
*Assistant Examiner* — Marjan Fardanesh
(74) *Attorney, Agent, or Firm* — Laubscher & Laubscher, P.C.

(57) ABSTRACT

A signal acquisition circuit detects a wanted signal in a composite signal containing the wanted signal and an unwanted signal, where the highest frequency in the unwanted signal is higher than the highest frequency in the wanted signal. A sensor captures the composite signal and an analog-to-digital converter samples and converts the composite signal to digital format, and a filter subtracts the unwanted signal from the composite signal. The sampled signal contains a first component containing the sum of the wanted signal and the unwanted signal sampled at a first rate at least equal to the Nyquist rate for the wanted signal but less than a second rate that is at least equal to the Nyquist rate for the unwanted signal, and a second component containing the unwanted signal sampled at the second rate. The analog-to-digital converter outputs to the filter a first digital signal containing the first component sampled at the first rate and a second digital signal containing the second component at the second rate. The circuit is useful for detecting a photoplethysmograph signal in the presence of ambient light in a pulse oximetry sensor.

28 Claims, 3 Drawing Sheets

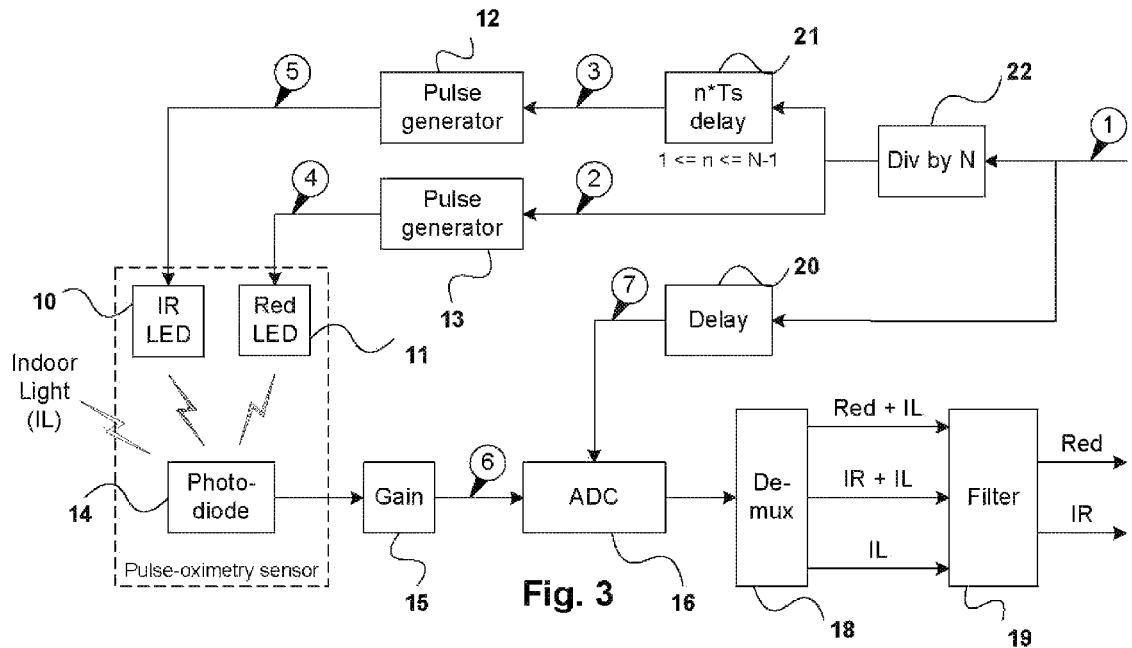
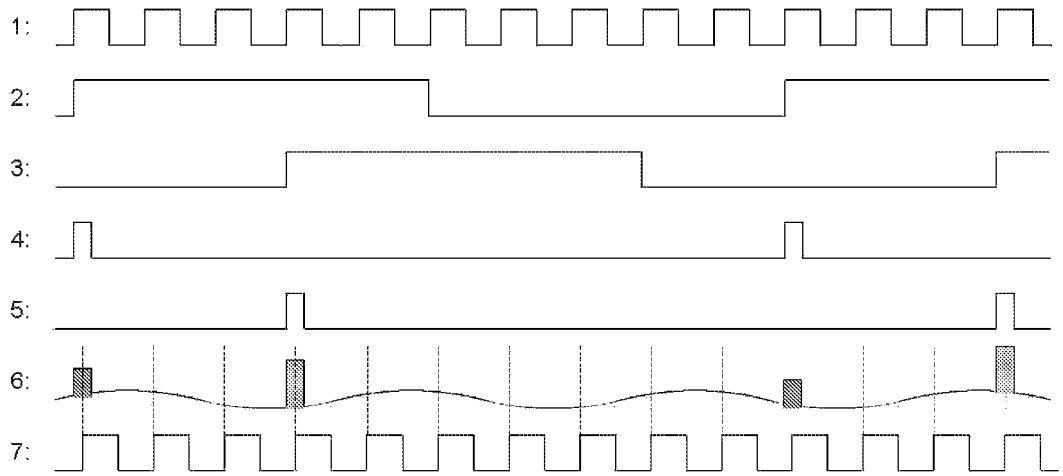
Note: Timing diagram for N = 10 and n = 3
Fig. 4

SIGNAL ACQUISITION CIRCUIT FOR DETECTING A WANTED SIGNAL IN THE PRESENCE OF AN UNWANTED SIGNAL

FIELD OF THE INVENTION

This invention relates to the field of signal processing, and in particular to an acquisition circuit for detecting a wanted signal in the presence of an unwanted signal, for example, in a pulse oximetry sensor.

BACKGROUND OF THE INVENTION

Pulse oximetry is a non-invasive method allowing the monitoring of the oxygenation of a patient's hemoglobin. A sensor is placed on a thin part of the patient's body, usually a fingertip or earlobe. Light of different wavelengths (red and infrared) is sequentially passed from one side to a photodiode on the other side. Changing absorbance of each of the two wavelengths is measured, allowing determination of the absorbances due to the pulsing arterial blood alone.

Traditionally, in a pulse-oximetry sensor, LED's are flashed at the same rate as the photodiode sampling rate. For a pulse-oximetry system to be able to remove indoor light artifacts, this rate needs to be at least 100/120 Hz, i.e. above the Nyquist frequency of the fundamental of indoor light (50/60 Hz), and more likely above 200/240 Hz given the first harmonic is often the dominant component. See, for example, "Artificial Lighting Interference on Free Space Photoelectric Systems", Maximilian Hauske et al, EMO '09/Kyoto, 2009, paper 21 P3-1.

The acquired signal fully describes both wanted and unwanted indoor light information and allows for the separation of the two using digital filtering. At that flashing rate the LED's account for most of the power consumption of the pulse-oximetry sensor, which is in the order of 10 mW. If harmonics of the indoor light need to be removed as well (e.g. in case of fluorescent light, second and third harmonics can be significant), the sampling rate needs to be increased, with an equivalent effect on the power consumption.

As long as the power consumption of the sensor is not a critical parameter, the above-mentioned implementation is the simplest. An example of such an implementation is given in FIG. 1. This comprises a divide-by-2 counter receiving a clock signal 1. This is passed through an inverter to a pulse generator driving a red LED and directly to a pulse generator driving an infrared LED.

The signal is picked up by the photodetector, and passed through an amplifier to an analog-to-digital converter (ADC) driven by the clock signal through a delay line. The output of the ADC goes to a demultiplexer, which separates the red and IR components. The output of the demultiplexer is passed through a filter to remove the background illumination IL.

A timing chart for the system is shown in FIG. 2. In this figure, trace 1 shows the base clock of the system, traces 2 and 3 show how the Red and IR, respectively, LED timing is generated from the base clock, traces 4 and 5 show the Red and IR, respectively, LED drive pulses, trace 6 shows the sensed Red and IR signals on top of the unwanted indoor light signal, and trace 7 shows the sampling time base, in this case a delayed base clock, and the ADC triggers (vertical dotted lines) indicating where the samples are taken.

For a body worn wireless sensor or simple $SpO_2$ monitor the power consumption of the LEDs in such a scheme is too large to be powered by a small battery such as a coin cell and still maintain an acceptable life-time.

SUMMARY OF THE INVENTION

According to the present invention there is provided a signal acquisition circuit for detecting a wanted signal in a composite signal containing the wanted signal and an unwanted signal, where the highest frequency in the unwanted signal is higher than the highest frequency in the wanted signal, comprising a sensor for detecting the composite signal; an analog-to-digital converter for sampling the composite signal at a high rate that is at least equal to the Nyquist rate for the highest frequency in the unwanted signal; a filter for subtracting the unwanted signal from the composite signal; and which is configured such that the analog-to-digital converter outputs a first component containing the sum of the wanted signal and the unwanted signal sampled at a low rate at least equal to the Nyquist rate for the wanted signal but less than the high rate and a second component containing the unwanted signal sampled at the high rate.

The invention is particularly useful in the field of pulse oximetry, although it will be appreciated that it has more general application as discussed below. For convenience, the invention will be exemplified in the field of pulse oximetry.

It will be understood that the term "circuit" is used in the most general sense, and includes a software implementation, for example, using a signal processor.

The invention is based in part on the realization that in a pulse oximetry sensor the photoplethysmograph signal, from which blood oximetry is derived, is contained within a 5 Hz bandwidth, i.e. an order of magnitude below the fundamental of indoor light and from the fact that the LEDs are not needed to capture the ambient light information. The LED flashing rate therefore does not need to be the same as the sampling rate. A flashing rate of 10 Hz, i.e. the Nyquist rate of the photoplethysmograph signal, is sufficient. Typically, the flashing rate would be less than 20 Hz.

The sampling must be such that enough information about the unwanted light signal is acquired during the time the LED's are not on. By decorrelating LED flashing (the dominant component in power consumption) and photodiode sampling, a power saving factor in the order of 10 can be achieved. It will be appreciated that this principle can be applied more generally to any situation where a wanted signal has a lower bandwidth than an unwanted signal.

The invention also provides a pulse oximetry sensor comprising at least two light sources; a pulse generator arrangement for sequentially pulsing said light sources at a low rate that is at least equal to the Nyquist rate of a photoplethysmograph signal but less than a high rate at least equal to the Nyquist rate for the highest frequency of the ambient light to be removed; a photodetector for detecting light pulses from said light sources in the presence of artificial ambient light; an analog-to-digital converter (ADC) triggered at the high rate for converting an output of the photodetector to digital format, wherein the analog-to-digital converter outputs a composite output signal having a first component containing the signals from the light pulses in the presence of ambient light sampled at the low rate and a second component containing an ambient light signal sampled at the high rate; a demultiplexer for separating said signals; and a filter downstream of the demultiplexer for subtracting the ambient light signal from each of the signals from the light pulses in the presence of ambient light.

In one embodiment, a pair of light sources is provided, but there could be more. Typically, the first component will contain the signal Red+IL, and IR+IL, where Red+IL is the wanted signal from a red light source plus the ambient light and which are independent of each other, and IR+IL, where IR is the signal from the an infrared light source. These signals are of course independent of each other.

BRIEF DESCRIPTION OF THE DRAWINGS

The invention will now be described in more detail, by way of example only, with reference to the accompanying drawings, in which:—

FIG. 3 is a block diagram of a prior art pulse-oximetry sensor in accordance with an embodiment of the invention;

FIG. 4 is a timing chart for the circuit shown in FIG. 3;

DETAILED DESCRIPTION OF THE INVENTION

Figure 1:
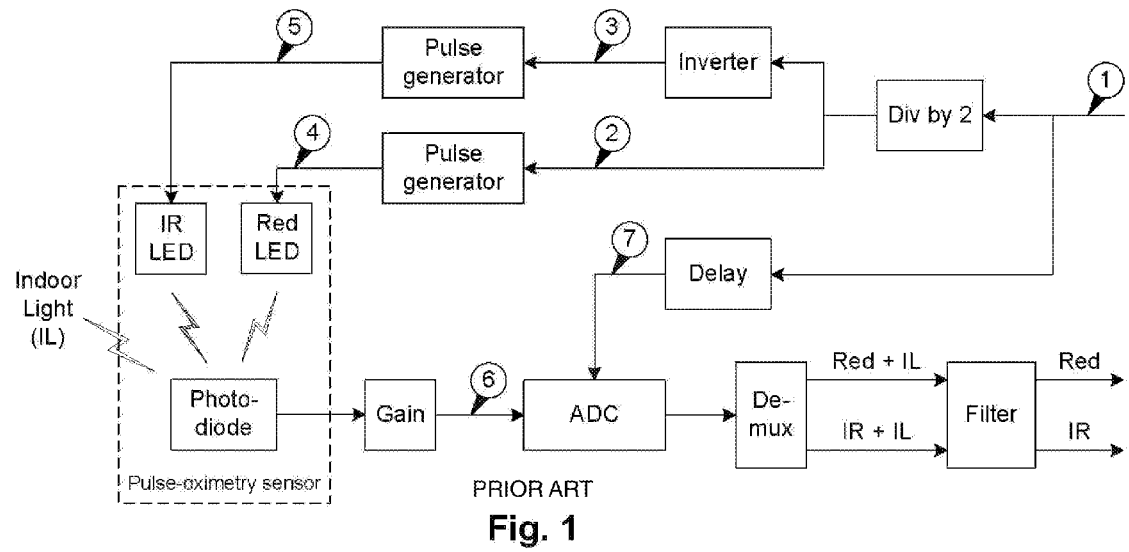
FIG. 1 is a block diagram of a prior art pulse-oximetry sensor.

The pulse oximetry sensor in FIG. 3 is similar to FIG. 1 in that it has red and IR LEDs 10, 11 driven by pulse generators 12, 13. The light signals are picked up by the photodetector 14 and passed through amplifier 15 to ADC 16 driven by the clock signals 1 through the delay line 20. In a general sense the assembly comprising the LEDs 10, 11 and photodetector 14 may collectively be regarded as the pulse oximetry sensor.

The clock signals 1 are also passed through a divide-by-N counter 22, where N is an integer, for example 10. The output of the divide-by-N counter 22 is passed directly to the pulse generator 13 for the IR LED and through n*Ts delay line 21, where Ts is the base clock period and 1≤n≤N−1.

The output of the ADC is passed to demultiplexor 18, which produces three signals, RED+IL, IR+IL, and IL, where IL is the background illumination. The filter 19 then removes the background illumination by subtracting the signal IL from the other two.

Figure 2:
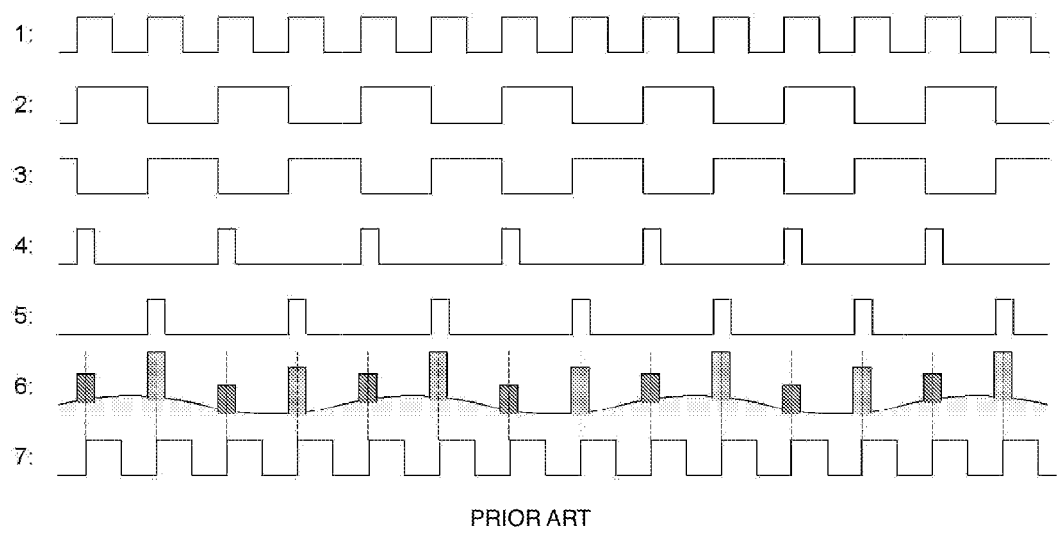
FIG. 2 is a timing chart for the circuit shown in FIG. 1.

As in the case for FIG. 2, in FIG. 4 trace 1 shows the base clock of the system, traces 2 and 3 show how the Red and IR, respectively, LED timing is generated from the base clock, traces 4 and 5 show the Red and IR, respectively, LED drive pulses, trace 6 shows the sensed Red and IR signals (dark and light grey pulses) on top of the unwanted indoor light signal, and trace 7 shows the sampling time base, in this case a delayed base clock, and the ADC triggers (vertical doted lines) indicating where the samples are taken.

In the sampling scheme shown in FIG. 4, samplings are taken at the base clock rate, which in this example is ten times the pulse rate of the LEDs. FIG. 4 shows a sampling scheme where the indoor light signal is acquired in the period between the pulses containing the red and IR signals. These pulses contain the unwanted ambient light signal, but unlike the prior art, the signal detected between these pulses only contains the unwanted ambient signal, which can be detected and removed by subtraction. The pulse oximetry sensor, which consists of the assembly of the LEDs and photodiode, is effectively enabled or gated to pick up the composite signal comprising the LED light and the ambient light by the pulsing of the LEDs 10, 11.

In FIG. 4, the unwanted signal is detected in phase with the red and IR samples. In an alternative sampling scheme the indoor light signal may be acquired 180 degree of phase of the red and infrared sampling.

While the invention has been described in connection with pulse-oximetry, it is applicable to any acquisition system where the sampling rate is dictated by unwanted signal, where the highest frequency of the unwanted signal is higher than the highest frequency of the signal of interest and where energy must be expended to make the wanted signal observable by the system, typically in a sensor or part of a sensor. Other examples include pressure or temperature sensors using a Wheatstone bridge circuit. In this example, the signal obtained from such a circuit would be the combination of a pressure or temperature resistor, three independent resistors, and power applied to the circuit. In this case the wanted signal, the pressure, might be contaminated by an unwanted signal injected in the analog gain stage. By using the pulse generator to power the Wheatstone bridge, sampling of the pressure signals (contaminated by the unwanted signal) can be carried out at a lower rate than the sampling of the unwanted signal in the same manner as the pulse oximetry sensor. Another type of sensor that could be used would be a powered microphone. The microphone can be powered at intervals to allow the principles of the invention to be applied to remove an unwanted interfering signal.

Figure 5:
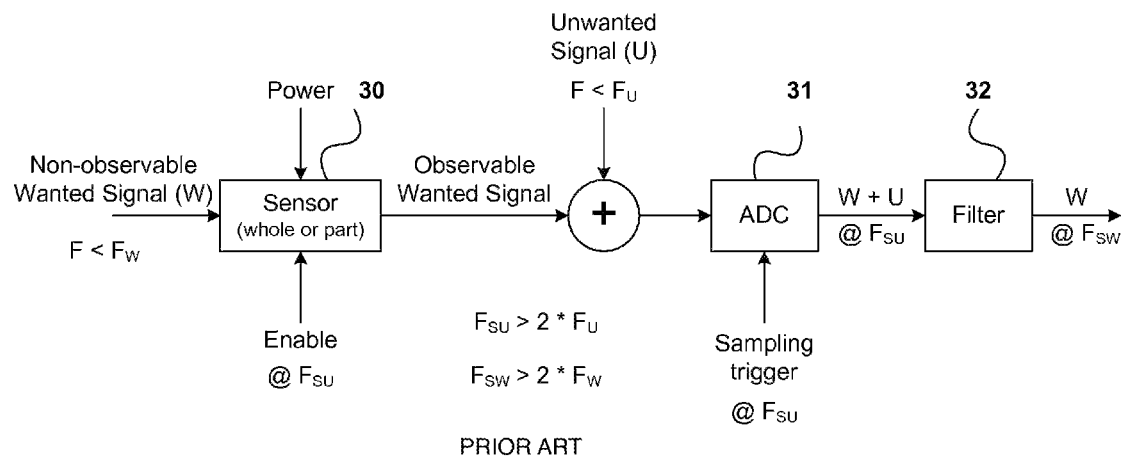
FIG. 5 shows a generic sensor system to which the invention is applicable.

FIG. 5 illustrates a generic system of this nature. The wanted signal W picked up by sensor 30, which as noted in the example of the pulse oximetry device consists of the LED light sources and the photodiode, contains an unwanted signal F. Despite the fact that the wanted signal W can be fully represented with a sampling rate $F_{SW}$, the whole acquisition up to the output of filter 32 runs on a higher sampling rate $F_{SU}$ in order to avoid aliasing of the unwanted signal so as to be able to remove it from the acquired signal and extract the wanted signal. Once the higher frequency unwanted signal has been removed, the sampling rate can be reduced to $F_{SW}$ at the output of the filter 32. The timing chart for this system is similar to FIG. 2.

Figure 6:
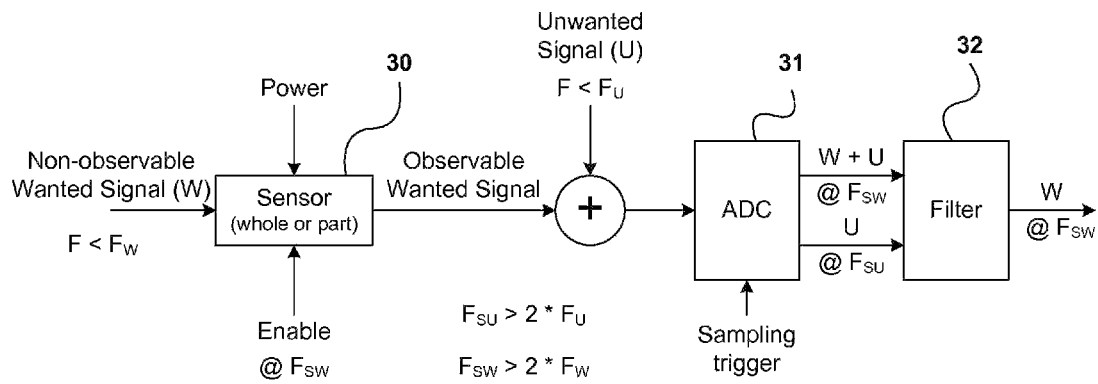
FIG. 6 shows the generic system of FIG. 5 modified in accordance with the invention.

FIG. 6 shows such a generic system embodying the present the invention. In this case, the sensing of the wanted signal is now performed at the lower sampling rate $F_{sw}$, which is at least equal to the Nyquist rate for the wanted signal, but less than the Nyquist rate for the unwanted signal. Because this is often the most power demanding step in the whole acquisition process, the overall power consumption can be greatly reduced.

The sampled signal has now two components: 1) the sum of the wanted and the unwanted signals at a sampling rate $F_{SW}$ and 2) the unwanted signal at a sampling rate $F_{SU}$. The sampling rate of the unwanted signal does not need to be regular; it only needs to fulfil the requirements of signal theory to gain sufficient information about the original unwanted signal for the purpose of recovering the wanted signal and whatever further requirements, if any, imposed by the filter implementation. This statement is also true of the wanted signal. The sampling rate of the wanted signal need not be regular so long as it fulfils the requirement of signal theory to provide a full representation of the original signal and meet any requirements imposed by the filter implementation.

The sensing of the ambient signal could be performed independently with a different sensor and added to the composite signal in an adder as illustrated, or as was the case in the FIG. 3 embodiment, the same sensor could of course detect both the composite and unwanted signal, in which case the addition occurs in the sensor. In this case the lower sampling rate for the composite signal can be brought about by pulsing the source of the wanted signal at the lower rate.

In the first component the wanted signal is fully represented but the unwanted signal is aliased. The second component adds the missing information about the unwanted signal, allowing the filter to remove it from the first component and extract the wanted signal only.

It should be appreciated by those skilled in the art that any block diagrams herein represent conceptual views of illustrative circuitry embodying the principles of the invention. The invention may be implemented on a processor, which may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. The term circuit is used herein to encompass functional blocks that may in practice be implemented in software. The invention could also be implemented in analog hardware.

The invention claimed is:

1. A signal acquisition circuit for detecting a wanted signal in a composite signal containing the wanted signal and an unwanted signal, where the highest frequency in the unwanted signal is higher than the highest frequency in the wanted signal, comprising:
 a first sensor arranged to sense the composite signal, the composite signal being sensed at a rate that is at least equal to the Nyquist rate for the highest frequency in the wanted signal and less than the Nyquist rate for the highest frequency in the unwanted signal;
 a second sensor arranged to sense the unwanted signal, without the wanted signal, at a rate that is at least equal to the Nyquist rate for the highest frequency in the unwanted signal;
 an analog-to-digital converter arranged to receive the outputs of the first sensor and the second sensor, and sample the received outputs of the first sensor and the second sensor at a sampling rate that is at least equal to the Nyquist rate for the highest frequency in the unwanted signal;
 a demultiplexer arranged to receive the output of the analog to digital converter and output a signal representative of the unwanted signal separately from a signal representative of the composite signal; and
 a filter arranged to subtract the output signal representative of the unwanted signal from the signal representative of the composite signal and thereby output a signal representative of the wanted signal. containing the sum of the wanted signal and the unwanted signal sampled at a low rate at least equal to the Nyquist rate for the wanted signal but less than the high rate and a second component containing the unwanted signal sampled at the high rate.

2. The signal acquisition circuit as claimed in claim 1, further comprising an active element for which energy must be expended to make the wanted signal observable by the first sensor, said active element being energized at the sensing rate of the first sensor.

3. The signal acquisition circuit as claimed in claim 1, wherein the sensing of the second sensor is regular but intermittent.

4. The signal acquisition circuit as claimed in claim 1, wherein the sensing of the second sensor is irregular.

5. The signal acquisition circuit as claimed in claim 1, wherein the sensing of the first and second sensors are in phase with each other.

6. The signal acquisition circuit as claimed in claim 1, wherein the sensing of the first and second sensors are out of phase with each other.

7. The signal acquisition circuit as claimed in claim 1, wherein the first and second sensors are provided by a common sensor element.

8. The signal acquisition circuit as claimed in claim 1, wherein the first and second sensors are provided by a common sensor element, and further comprising an active element for which energy must be expended to make the wanted signal observable by the single sensor, said active element being energized at the sensing rate of the first sensor, and the common sensor element being the second sensor when said active element is not energized.

9. A method of acquiring a wanted signal in a composite signal containing the wanted signal and an unwanted signal, where the highest frequency in the unwanted signal is higher than the highest frequency in the wanted signal, comprising the steps of:
 sensing the composite signal at a low rate that is at least equal to the Nyquist rate for the highest frequency in the wanted signal but less than the Nyquist rate for the highest frequency in the unwanted signal;
 sensing the unwanted signal, without the wanted signal, at a rate that is at least equal to the Nyquist rate for the highest frequency in the unwanted signal;
 sampling said composite and unwanted signals at a sampling rate that is at least equal to the Nyquist rate for the highest frequency in the unwanted signal;
 producing a signal representative of the unwanted signal separately from a signal representative of the composite signal; and
 subtracting the signal representative of the unwanted signal separately from the signal representative of the composite signal to produce the wanted signal;
 wherein said sensing includes expending energy to make said wanted signal observable.

10. The method as claimed in claim 9, wherein said composite signal and said unwanted signal are sensed in separate sensors.

11. The method as claimed in claim 9, wherein said composite signal and said unwanted signal are sensed in a common sensor element.

12. A method as claimed in claim 9, wherein the sampling sensing of the unwanted signal is regular but intermittent.

13. A method as claimed in claim 9, wherein the sensing of the unwanted signal is irregular.

14. A method as claimed in claim 9, wherein the sensing of the composite signal is in phase with the sensing of the unwanted signal.

15. A method as claimed in claim 9, wherein the sensing of the composite signal is out of phase with the sensing of the unwanted signal.

16. A pulse oximetry sensor comprising:
 a first and a second light source;
 a pulse generator arrangement for sequentially pulsing said first and second light sources at a low rate that is at least equal to the Nyquist rate of a photoplethysmograph signal but less than a high rate at least equal to the Nyquist rate for the highest frequency of the ambient light to be removed;
 a photodetector for detecting light pulses from said first and second light sources in the presence of artificial ambient light and the ambient light in the absence of the light pulses from said light sources;

an analog-to-digital converter (ADC) triggered at the high rate for acquiring and converting an output of the photodetector to digital format, wherein the analog-to-digital converter outputs a signal having a first component containing the signals from the pulsed first and second light sources in the presence of ambient light sampled at the low rate and a second component containing the ambient light signal sampled at the high rate;

a demultiplexer for separating said first and second components into:
  a first signal representative of pulsed first light source;
  a second signal representative of the pulsed second light source; and
  a third signal representative of the ambient light; and
    a filter downstream of the demultiplexer for subtracting the third signal representative of the ambient light signal from each of the first and second signals light to output a first output signal representative of the pulsed first light source and a second output signal representative of the pulsed second light source.

17. A pulse oximetry sensor as claimed in claim 16, further comprising an input for receiving a base clock signal, and a divide-by –N unit for dividing the base clock signal by N, where N is an integer, and wherein said pulse generator arrangement comprises a first pulse generator for driving the first light sources receiving the output of the divide-by-N unit, and a second pulse generator for receiving a delayed version of the output of the divide-by-N unit for driving the second light sources, and a delay unit for applying a delayed version of the base clock signal to a trigger input of the ADC.

18. A pulse oximetry sensor as claimed in claim 17, which is configured such that the delay applied to the output of the divide-by-N unit before application to the second pulse generator is given by the expression n*Ts where Ts is the base clock period and n is within the range $1 \leq n \leq N-1$.

19. A pulse oximetry sensor as claimed in claim 18, which is configured such that the ambient light in the absence of the light pulses from said light sources is converted in the gaps between signals from the first and second light sources.

20. A pulse oximetry sensor as claimed in claim 17, which is configured such that the trigger for the ADC for the acquiring of the detected light pulses from said first and second light sources in the presence of artificial ambient light is 180 degrees out of phase with the trigger for the acquiring of the ambient light in the absence of the light pulsed.

21. A pulse oximetry sensor as claimed in claim 17, wherein the first light source and the second light source emit respectively at red and infrared wavelengths, and wherein N=10, and wherein said high rate is approximately equal to said base clock rate, which is ten times the pulse rate of said light sources.

22. A pulse oximetry sensor as claimed in claim 17, wherein the low rate is at least 10 Hz and less than 100 Hz.

23. A method of acquiring a wanted signal in a pulse oximetry sensor comprising:
  sequentially pulsing a first and a second light sources, having different effective wavelengths, at a first rate that is at least equal to the Nyquist rate of a photoplethysmograph signal but less than a second rate at least equal to the Nyquist rate for the highest frequency of an ambient light to be removed;
  detecting light pulses from said first and second light sources in the presence of the ambient light and further detecting ambient light in the absence of light pulses from the first and second light sources to produce a composite signal;
  acquiring and converting said composite signal to digital format in an analog-to-digital converter triggered at the second rate to produce an converted signal having a first component representative of the detected light pulses from the first light source in the presence of ambient light, a second component representative of the detected light pulses from the second light source in the presence of ambient light and a third component representative of the detected ambient light and second light sources in the absence of light pulses from the first and second light sources;
  separating said components of the signal; and
  subtracting the third component from each of the first and second components to output a first signal representative of the pulsed signal of the first light source and a second signal representative of the pulsed signal of the second light source.

24. A method as claimed in claim 23, further comprising receiving a base clock signal, dividing the base clock signal by N to produce a divided signal, where N is an integer, and pulsing the first light sources by the divided signal and the second light sources by a delayed version of the divided signal, and triggering the analog-to-digital converter with a delayed version of the base clock signal.

25. A method as claimed in claim 24, wherein the second light sources is pulsed by the divided signal delayed by n*Ts where Ts is the base clock period and n is within the range $1 \leq n \leq N-1$.

26. A method as claimed in claim 23, wherein the ambient light signal is acquired in the gaps between signals from the first and second light sources.

27. A method as claimed in claim 23, wherein the trigger for the acquiring of the analog-to-digital converter for the acquisition of the composite signal having detected light pulses from the first and second light sources is 180 degrees out of phase with the trigger for the acquisition of the ambient light.

28. A method as claimed in claim 23, wherein the low rate is at least 10 Hz and less than 100 Hz.

* * * * *